United States Patent [19]
Bao et al.

[11] 4,051,713
[45] Oct. 4, 1977

[54] FRICTION MEASURING AND TESTING METHOD AND APPARATUS

[75] Inventors: Frank W. Bao, Clermont, Fla.; James L. Hummeldorf, Morningview; Stephen D. Parker, Erlanger, both of Ky.

[73] Assignee: Actus, Inc., Florence, Ky.

[21] Appl. No.: 669,594

[22] Filed: Mar. 23, 1976

[51] Int. Cl.$^2$ .......................................... G01N 19/02
[52] U.S. Cl. ............................................... 73/9
[58] Field of Search ...................................... 73/9, 10

[56] References Cited
U.S. PATENT DOCUMENTS
2,269,305  1/1942  Bell ............................................ 73/9

FOREIGN PATENT DOCUMENTS
1,339,078  8/1963  France ....................................... 73/9

Primary Examiner—S. Clement Swisher
Attorney, Agent, or Firm—Fleit & Jacobson

[57] ABSTRACT

A method and apparatus for measuring or testing static and dynamic coefficients of friction. The frame of the apparatus is held fixed with respect to the test surface, and a friction pad, mounted on the frame and capable of moving relative to the frame, also rests on the test surface. A torque is developed in the friction pad, through the means of a fluid bed, and the resulting relative movement between the test surface and the friction pad is sensed. Also disclosed are mechanisms for setting the normal force which the friction pad exerts on the test surface, for adjusting to misalignments and small surface irregularities without deleterious effects, and for regulating the torque developed in the friction pad.

14 Claims, 8 Drawing Figures

FRICTION MEASURING AND TESTING METHOD AND APPARATUS

BACKGROUND OF THE INVENTION

The present invention relates generally to the field of friction measuring, or testing, and in particular to a method and apparatus for measuring the static and dynamic coefficients of friction of a surface. The method and apparatus also find use in measuring or testing the quality of lubricants.

Friction measuring devices are known to the prior art. They generally operate by developing linear forces between the surface under test and a bearing pad. The force necessary to move the bearing pad relative to the test surface is utilized to determine the coefficient of friction.

While these known devices are, to some extent, useful in developing information about static coefficient of friction, they are substantially useless insofar as tracing dynamic characteristics. These devices also tend to be somewhat inaccurate when measuring static coefficient of friction, because this characteristic is determined at a time when there is an abrupt breakaway of the friction pad from the test surface. Furthermore, the known devices are generally bulky and heavy, detracting from portability, and are sensitive to misalignments and surface irregularities.

The present invention is directed to an advanced method and apparatus for measuring or testing static and dynamic coefficient of friction, which overcome each of the disadvantages and drawbacks of known prior art techniques.

SUMMARY OF THE INVENTION

The present invention relates to a friction measuring and testing apparatus which is compact, lightweight, and capable of accurately measuring both static and dynamic coefficient of friction. The present invention also relates to a method for measuring and testing static and dynamic coefficient of friction.

In a specific embodiment, the inventive device comprises a small frame which firmly sits, by gravity, on the surface under test. A motor is mounted on the frame, and serves to generate a torque on a friction pad which is in contact with the test surface. This torque is transmitted from the motor shaft to the friction pad through the means of a fluid bed, thereby urging the pad to rotate relative to the test surface. The static and dynamic coefficient of friction characteristics of the test surface are determined by sensing the instant the pad breaks away from the test surface, and by monitoring the dynamic torque on the friction pad, once breakaway has occurred, and the rotational speed of the friction pad relative to the test surface.

The inventive device includes a rubber pad mechanism which ensures that the friction pad sits firmly on the test surface. Also provided is a mechanism for receiving weights to set the normal force of the friction pad on the test surface. The invention further includes feedback circuitry for controlling motor speed in accordance with a predetermined torque schedule. Output apparatus is also provided to display, record or store static and dynamic coefficient of friction characteristics.

It is accordingly one object of the present invention to provide an improved method and apparatus for measuring and testing the coefficient of friction of surfaces or the like.

A further object of the present invention is to provide a friction measuring and testing method and apparatus capable of determining both static and dynamic coefficient of friction characteristics.

Another object of the present invention is to provide an apparatus for measuring and testing coefficient of friction, which is compact, light in weight, and therefore portable.

Still a further object of the present invention is to provide a friction measuring and testing apparatus which is smooth in operation, and which therefore operates with great accuracy.

Yet another object of the present invention is to provide a method and apparatus for friction measuring and testing which relies upon the interaction of two surfaces through the means of a fluid bed.

Still a further object of the present invention is to provide a friction measuring and testing apparatus which is insensitive to misalignment and surface irregularities, and which can measure and test at different normal forces.

These and other objects of the present invention, as well as many of the attendant advantages thereof, will become more readily apparent when reference is made to the following description, taken in accordance with the accompanying drawings.

DETAILED DESCRIPTION OF THE DRAWINGS

Figure 1:
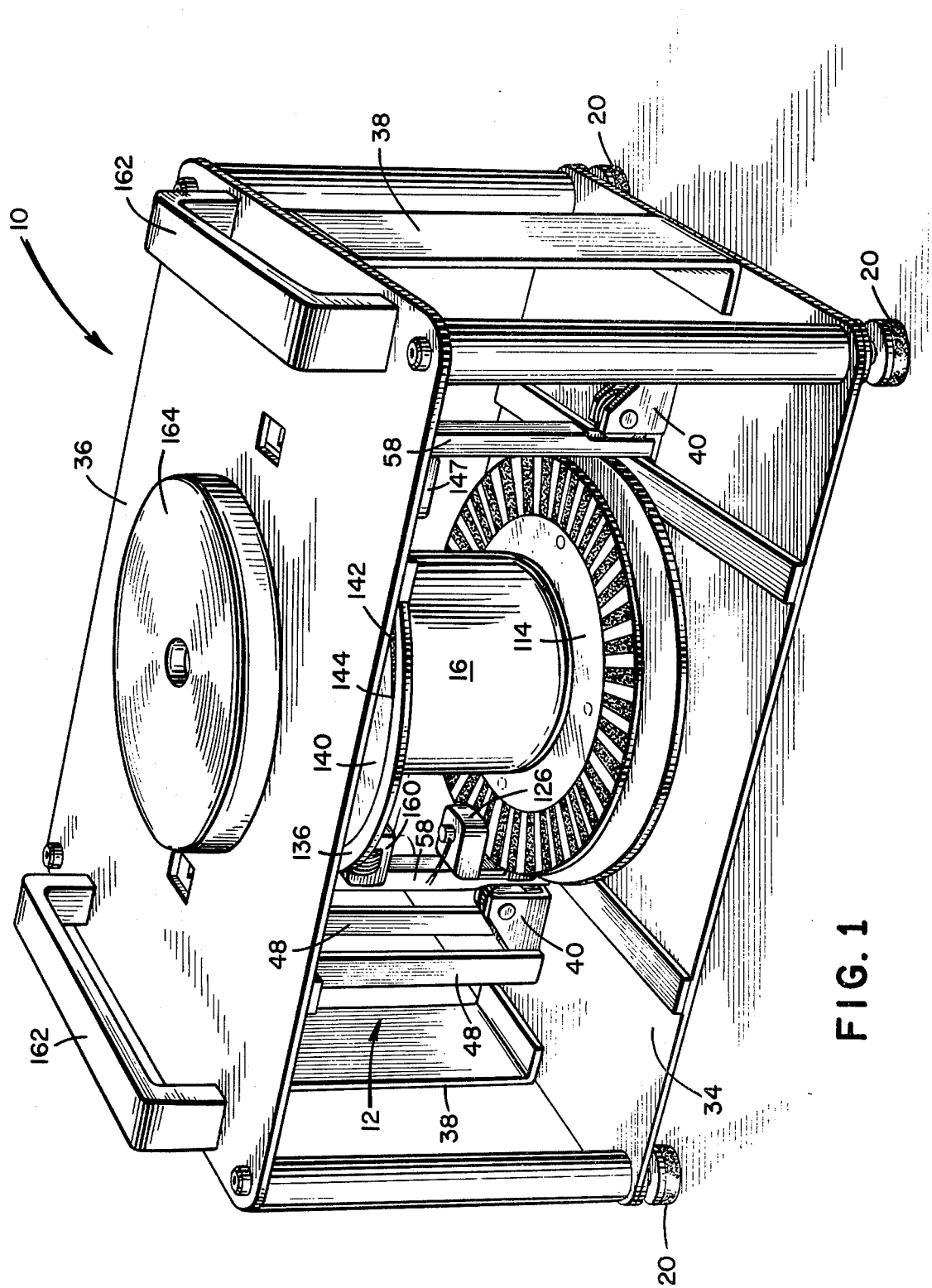
FIG. 1 is a front perspective view of the inventive measuring and testing device.
Figure 2:
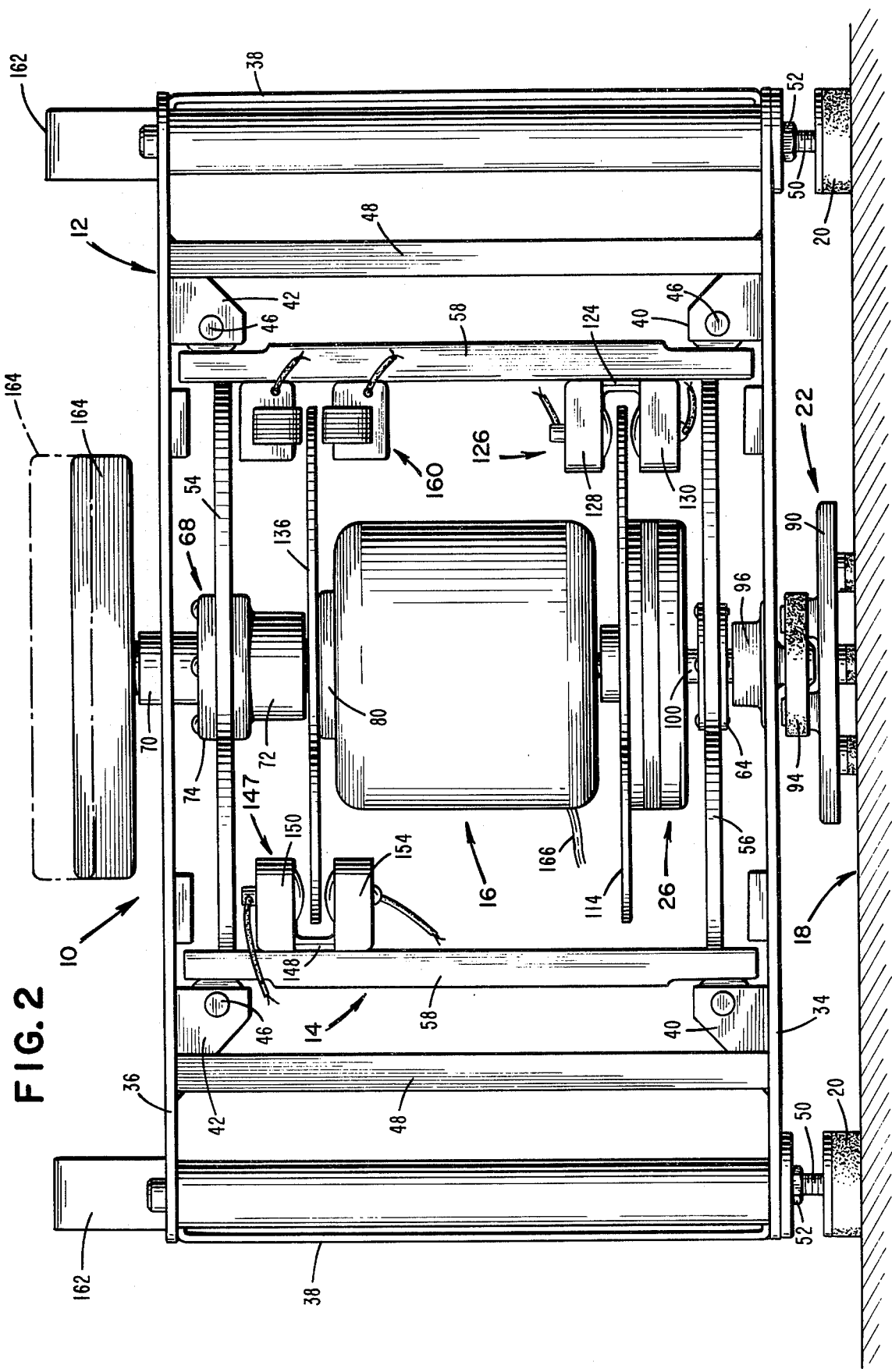
FIG. 2 is a rear plan view of the inventive measuring and testing device.

With reference first to FIG. 1 through 5, the structural configuration of the inventive device for measuring and testing will be described. The inventive measuring and testing device is shown generally at 10 and comprises an outer frame 12, a housing cage 14 mounted on the outer frame 12, and a motor 16 mounted in the housing cage 14. The outer frame 12 is rectangular in plan view and sits on the test surface 18 through four rubber feet 20. A friction pad 22 is movably mounted in outer frame 12, and also sits on the test surface 18, through rubber feet 24. The upper region of the friction pad 22 is fixed to a fluid housing 26, which is filled with a viscous fluid 28 and which houses a disc 30. The disc 30 is, in turn, connected to motor 16 through motor shaft 32.

The outer frame 12 comprises a rectangular lower support plate 34 and an upper support plate 36. Support plates 34 and 36 are connected to one another at their four corners by means of corner struts 38. Two roller flanges 40 are fixed relative to the lower support plate 34, and two flanges 42 are fixed relative to the upper support plate 36, the aligned roller flanges 40 and 42 being in vertical pairs. Each roller flange 40 and 42 is equipped with a roller 44 adapted to turn about a shaft 46. Alignment braces 48 are shown as mounts for the respective roller flanges 40 and 42, to ensure alignment and to add further support between the lower and upper support plates 34 and 36. The four rubber feet 20 are mounted on the lower support plate 34 through the means of threaded bolts 50, each held in place by upper and lower nuts 52. Nuts 52 are preferably secured to the lower support plate 34, so that each rubber foot 20 can be adjusted by turning its bolt 50 relative to the lower support plate 34.

The housing cage 14 comprises an upper support plate 54, a lower support plate 56, and at least two vertical support struts 58 which rigidly connect upper and lower support plates 54 and 56, respectively. Though not illustrated, the surface of the struts 58 which face rollers 44 are V-shaped in the vertical direction so that the housing cage 14 is vertically moveable by aligned association with rollers 44. The lower support plate 56 is apertured, as shown at 60, to support a thrust bearing 62 affixed to support plate 65 by means of bolted bearing clamps 64.

The upper support plate 54 is also centrally apertured, as shown at 66, and serves as a base for a motor mount shown generally at 68. Motor mount 68 includes an upper mount 70 and a lower mount 72, connected together by means of bolts passing through the support plate 54. A torsion rod 76 extends through support plate 54 and is fixed relative to upper mount 70 by means of set screws 78. The lower portion of torsion rod 76 is fixed to a mounting bracket 80 integral with motor 16 through the means of set screws 82. The lower mount 72 is internally hollow, and accepts the neck 84 of mounting bracket 80. A retaining collar 86 holds motor 16, through its mounting bracket 80, to the motor mount 68, and rotation of the motor 16 relative to motor mount 68 is permitted by means of a bearing 88. Torsion rod 76 prevents free rotation of motor 16 relative to motor mount 68, but enables motor rotation through approximately 180°.

The friction pad 22, as noted above, sits on test surface 18 through the means of rubber feet 24. For purposes of alignment with surface 18, three feet 24 are provided. Friction pad 22 comprises a generally horizontal main body 90 having at least two upwardly extending tabs 92. These tabs 92 serve to support an apertured rubber alignment pad 94 which, in turn, is connected to a housing support 96 through the means of support tab 98. Housing support 96 connects the fluid housing 26 to the friction pad 22 by way of a pin 100 fixed both to the bottom of fluid housing 26 and to the top of housing support 96. The thrust bearing 62 permits rotation of pin 100 relative to the lower support plate 56 of the housing cage 14.

The fluid housing 26, as noted above, is filled with a fluid 28, for example, a high viscosity silicon grease. As illustrated, the housing 26 comprises a lower body 102, an upper body 104, and a spacer gasket 106. The fluid housing 26 is circular in cross section, and defines a cylindrical interior chamber 108. It is this chamber 108 which houses fluid 28.

Figure 4:
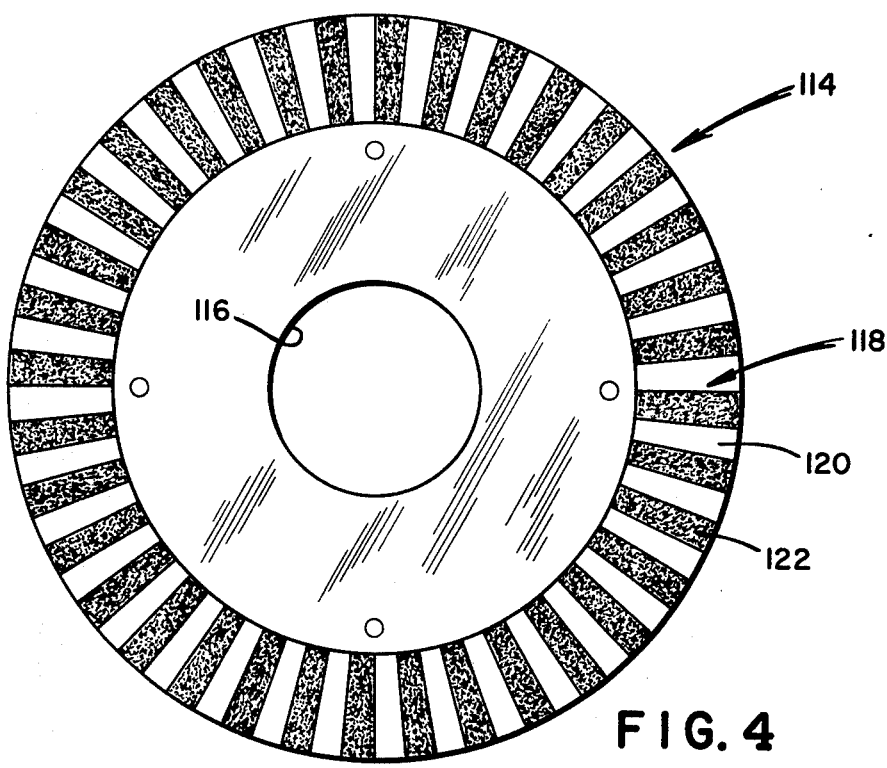
FIG. 4 is a plan view of the speed reticle used in the inventive device.
Figure 5:
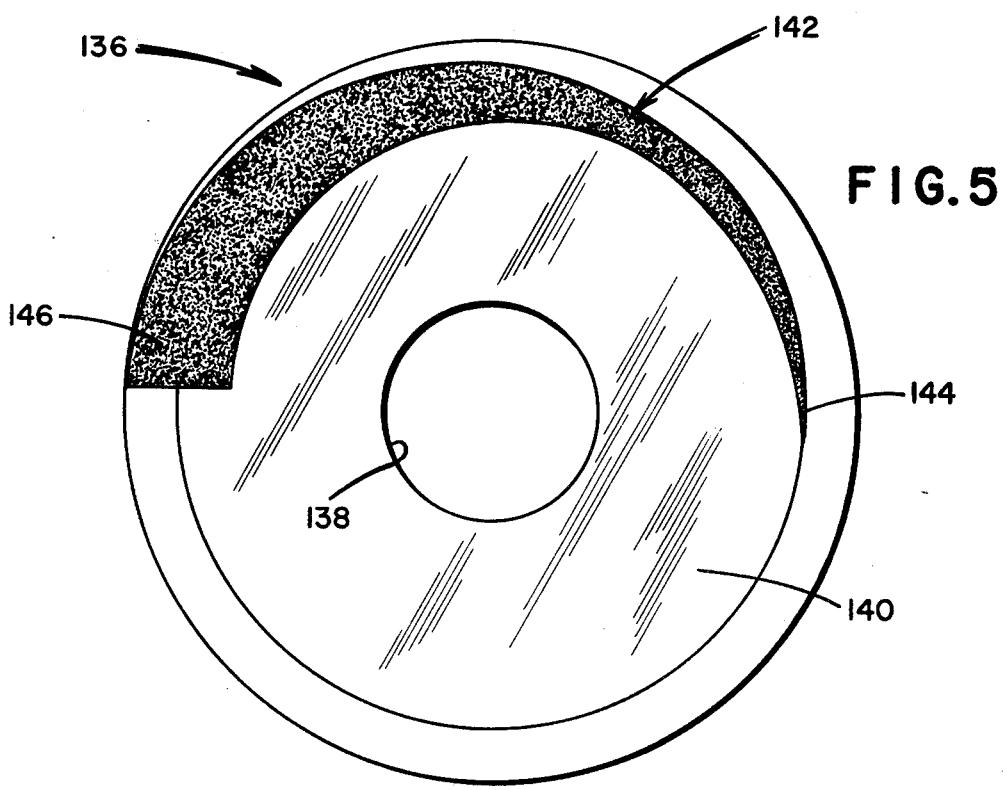
FIG. 5 is a plan view of the torque reticle used in the inventive device.

Upper body 104 of fluid housing 26 is centrally apertured at 110, and includes a seat for bearing 112. The motor shaft 32 passes through aperture 110, with its bearing 112, and is fixed to the disc 30, centrally aligned in chamber 108. A speed reticle 114, best illustrated in FIG. 4, is affixed to the upper surface of fluid housing 26. Speed recticle 114 is apertured, at 116, to accept the neck of the upper body 104. Speed reticle 114 is preferably of a transparent material and, as best seen in FIG. 4, has an outer ring comprising alternating transparent and non-transparent strips. Specifically, the outer ring of speed reticle 114, shown generally at 118, comprises alternating transparent strips 120 and non-transparent strips 122.

Associated with speed reticle 114 is a speed detector shown generally at 126. Detector 126 comprises a tined mounting plate 124 bolted to a strut 58 of the housing cage 14. Mounting plate 124 has an upper tine 128 and a lower tine 130. Upper tine 128 serves as a mount for a light emitting diode 132, which emits light into a chamber 133, while lower tine 130 supports a photodiode shown at 134 which receives light from its chamber 135. Lenses 158 are provided for focusing the light. It should be evident that as speed reticle 30 rotates the continuous light emitted by diode 132 is received by photodiode 134 as pulses.

At the upper region of housing cage 24, and affixed to the horizontal surface of mounting bracket 80, is a torque reticle 136. Torque reticle 136 is apertured, as shown at 138 in FIG. 5, to accept the neck 84 of the mounting bracket 80. Torque reticle 36 is preferably of transparent material, as shown at 140, but includes a darkened, non-transparent masked region 42 extending near the periphery of reticle 136 for approximately 180°. Masked region 142 is narrow at end 144 and progressively widens through 180° to end 146.

Torque reticle 136 associates with a torque detector 147, which can be identical to speed detector 126. Torque detector 126 comprises a tined mounting plate 148 bolted to a strut 58, having an upper tine 150 which serves to mount a light emitting diode 152, and a lower tine 154 which supports a photodiode 156. Lenses 158 serve to focus the transmitted and received light. And as was the case with speed detector 136, torque detector 136 operates by sensing the amount of light which is transmitted from the continuously emitting diode 132, through the reticle and received by photodiode 156. However, rather than receiving a train of light pulses as does photodiode 134, photodiode 156 receives continuous light, the intensity of which is dependent upon the width of the masked region 142 between respective diodes 152 and 156.

It should be noted that while an optical torque measuring mechanism has been specifically disclosed, other techniques are available. For example, the motor unit could be mounted for axial rotation, but held in a "normal" position by a biasing spring or the like. Then, rotation of the motor unit from the "normal" position could be sensed through the means of a potentiometer.

Figure 3:
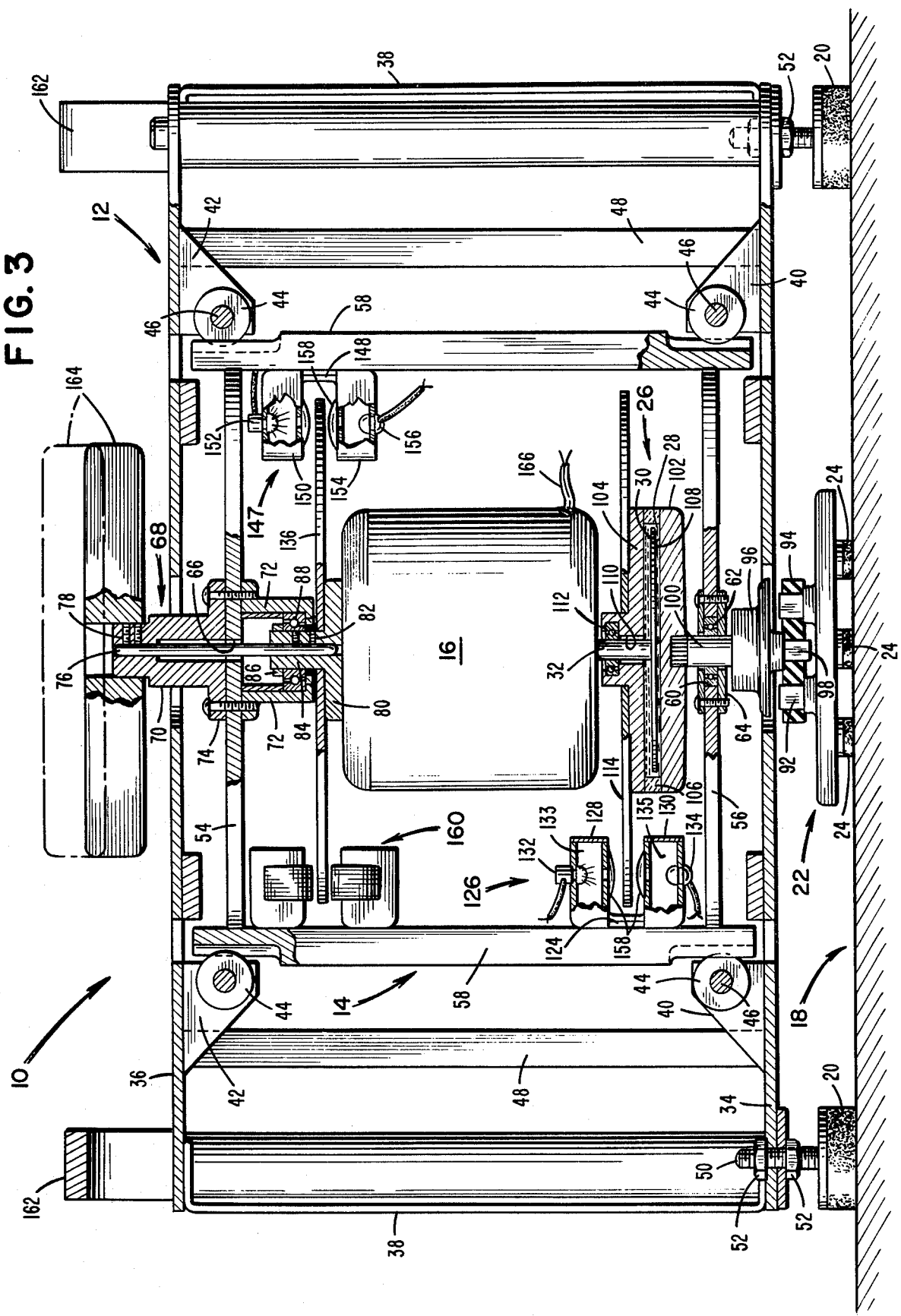
FIG. 3 is a front view, partially in section, of the inventive measuring and testing device.

Also illustrated in FIG. 3 is an eddy brake, shown generally at 160. Eddy break 160 is optional, requires that a portion of disc 136 be coated with a metallic material, and serves to dampen rotational oscillation of the motor, especially just after breakaway.

The basic operation of the invention measuring and testing apparatus is as follows. The device 10 is lifted, by its handles 162, and is placed on the surface whose coefficient of friction characteristics are being measured or tested. Rubber feet 20 are adjusted so that the outer frame 12 is rigid relative to the test surface 18. The friction pad 22 is also in contact with surface 18, with the normal force on surface 18 being determined by the weight of the friction pad 22, fluid housing 26, motor 16, motor mount 68 and, if desired, weights 164 which are adapted to be positioned over the neck of upper mount 70. The three-point design of the friction pad 22 and the presence of rubber alignment pad 94 between the friction pad and the fluid housing ensures that the friction pad 22 makes good contact with the test surface 18. It will be recalled that the housing cage 14 is vertically movable, by contacting rollers 44, and therefore good contact of the friction pad 22 with the test surface 18 is ensured even if the surface is not absolutely planar in the region of measurement. It should be noted that when in repose, the narrowist masked region 144 of torque reticle 136 is in alignment with the diodes of the torque detector 147.

Once the testing and measuring device 10 is in its desired orientation on the surface 18, the gear reduced DC motor 16 is energized, through its electrical leads 166. Motor shaft 32 turns, and therefore so too does disc 30 in the fluid filled chamber 108. The rotation of disc 30 in the high viscosity fluid 28 in chamber 108 causes a drag to be felt by the disc and reactive forces to be generated in the fluid. These reactive forces are then transmitted by the fluid 28 to the fluid housing 26, and therefore to its connected friction pad 22. When the motor 16 runs at low speeds, the friction pad remains stationary relative to the test surface 18. Still, reactive forces are developed, and these forces result in a torque which causes motor 16 to turn slightly relative to housing cage due to interconnecting torsion rod 76. This slight turning of the motor 166 relative to its housing cage 14 results in a lessening of the intensity of light passing from light emitting diode 152 to photodiode 156. The angular displacement of torque reticle 136, from its repose position is directly related to the torque on friction pad 22 which is felt by test surface 18. This displacement is sensed by monitoring the output of photodiode 156.

The speed at which motor 16 drives disc 30 is then gradually increased until such time that the reactive force acting on fluid housing 26 causes the friction pad 22 to break away from test surface 18. At this instant, the output of photodiode 156 is directly proportional to the static coefficient of friction of surface 18. The instant of breakaway is sensed by photodiode 134, which issues a pulse when the first masking strip 122 of the speed reticle crosses the light path between light emitting diode 132 and photodiode 134.

Then, to obtain a trace of dynamic coefficient of friction, it is desirable that the angular speed of the friction pad 22 increase linearly with time. That is, the angular acceleration of the friction pad 22 relative to the test surface 18 should be constant. This linearly can be accomplished by sensing the pulsatile output of photodiode 134, and regulating the speed of motor 16, through a feedback circuit, so that the pulsatile output linearly increases in frequency. Alternatively the angular acceleration could be held constant by maintaining a constant torque on the friction pad, sensed by the output of photodiode 134.

Figure 6:
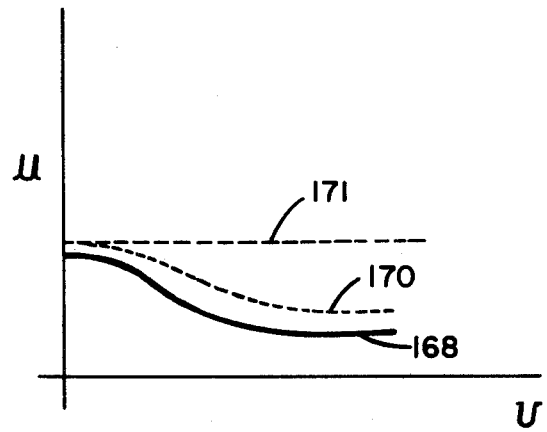
FIG. 6 represents two coefficient of friction curves, at differing normal forces, and showing both static and dynamic coefficient of friction characteristics.

FIG. 6 illustrates a curve of dynamic coefficient of friction which can be developed by utilizing the inventive apparatus. The ordinate represents the coefficient of friction, related to the output of photodiode 156 of torque detector 147, while the abscissa represents the angular velocity of speed reticle 114, related to the output of photodiode 134 of speed detector 126. Two curves are shown in FIG. 6. The lowermost curve 168 is a tracing of the dynamic coefficient of friction at a first normal force placed on the test surface by the friction pad. The curve 170 represents the dynamic coefficient of friction characteristics of the same surface, but with under a different normal force. Depending upon the characteristics of the surface, curve 170 could represent either a greater or lesser normal force. In any event, it should be appreciated that the illustrated curves are merely representative. The shape, slope, and sign of the slope all depend upon the particular surface being tested. The static coefficient of friction can be seen at 171, which is the coefficient of friction indicated on the ordinate at the instant when the speed reticle 114 commenses its rotation.

Figure 7:
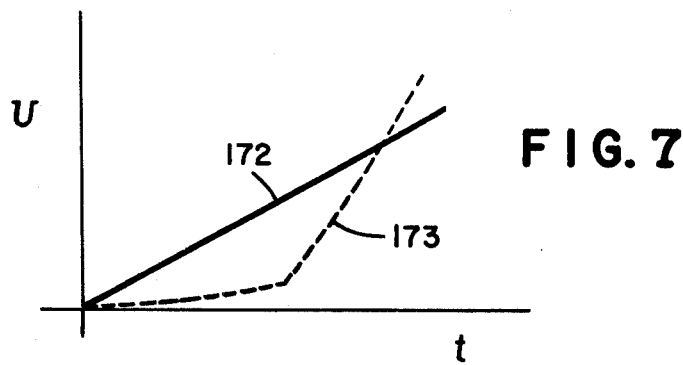
FIG. 7 is a curve of rotational velocity versus time showing the inventive device operating in its linear mode.

FIG. 7 illustrates a curve 172 showing a linear increase in the angular velocity of friction pad 22 relative to the test surface. It was noted above that this linear operation is desirable when developing the dynamic coefficient of friction curve shown in FIG. 6. However, linearity is not necessary. For example, FIG. 7 shows a curve 173 wherein the speed of the friction pad 22 is at first slowly increased (for greater accuracy in the region of breakaway), and is then accelerated at a greater rate.

Figure 8:
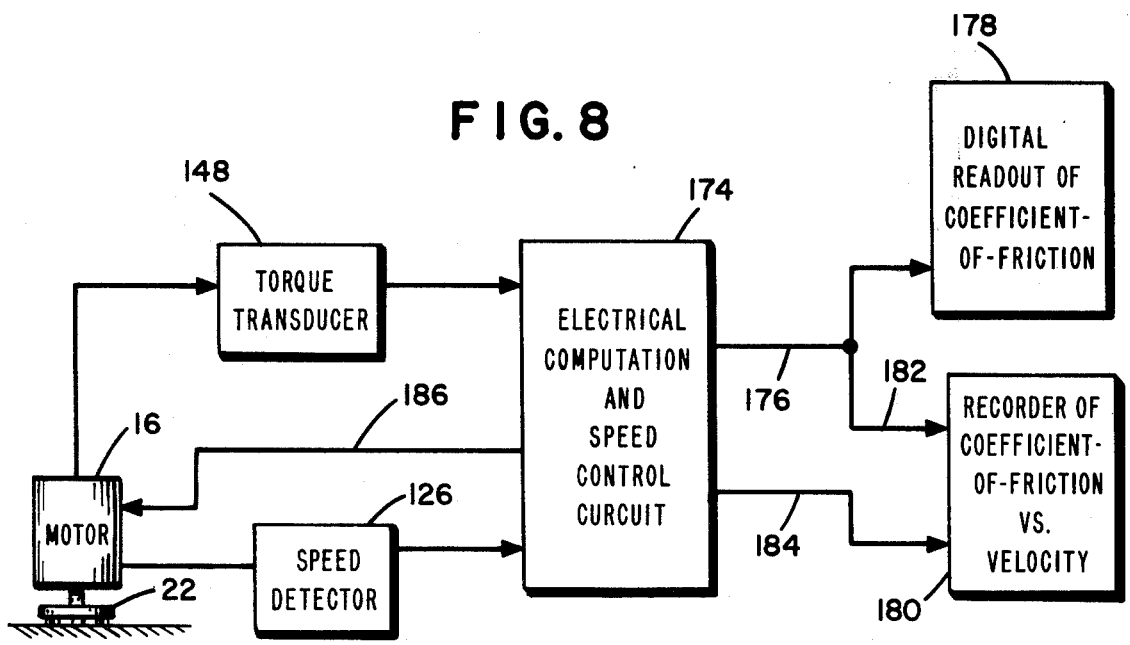
FIG. 8 is a block diagram of a circuit which is useful with the inventive measuring and testing device.

FIG. 8 shows a block diagram of a circuit useful with the inventive measuring and testing apparatus. In FIG. 8, the motor is illustrated at 16, and the friction pad at 22. The torque detector is shown at 148, and the speed detector at 126. It should be noted that FIG. 8 is merely schematic, for as described above, it is the output of photodiodes 154 and 134 which are representative of torque and speed, respectively. The output signals from the speed and torque detectors 126 and 148 are fed to an electrical computation and speed control circuit 174.

The function of circuit 174 is to receive the signals indicative of speed and torque, and to generate output signals which are compatable with the necessary inputs to the readout devices. In particular, one output of circuit 174 appears on line 176 and relates to torque information derived from torque detector 148. A digital readout of coefficient of friction is displayed by meter 178, the input of which was the signal on line 176. This same torque information is fed to a recording circuit 180, along line 182, along with a signal relating to the speed information received from the speed detector 126. This torque and speed input information is utilized by recording circuit 180 which generates a curve such as that shown in FIG. 6, namely the coefficient of friction plotted against velocity.

As noted previously, it is desirable that the velocity of the friction pad, or the torque, be controllable. In this regard, the circuit 174 is equipped with circuitry for reacting either to torque sensed by torque sensor 147 or to rotational speed sensed by speed detector 126. A motor control feedback signal is issued by circuit 174, on line 186, and is fed to motor 16 to control the speed thereof. It is contemplated that the electrical computation and speed control circuit 174 be capable of programming so that any curve of friction pad velocity versus time can be obtainable.

The foregoing description has made reference to rubber feet on the inventive device and to the base surface as the test surface. It should be appreciated that these terms are used for the sake of convenience, and are not intended to limit the flexibility of the present invention. The feet need not be rubber, but could be of any material, and the feet could be a material under test. Similarly the base surface could be a surface of known properties. The inventive device serves to test, or measure, static and dynamic coefficient properties between two surfaces in contact with one another.

Above, a specific embodiment of the present invention has been described. It should be appreciated, however, that this embodiment was described for purposes of illustration only, without any intention of limiting the scope of the present invention. Rather, it is the intention that the present invention be limited not by the above but only as is defined in the appended claims.

What is claimed is:

1. An apparatus for measuring and testing coefficient of friction characteristics of a surface and the like, the apparatus comprising: an outer frame adapted to be fixed relative to the surface under test; friction pad means mounted rotatably relative to said outer frame and adapted to contact the surface under test; a motor mounted on said outer frame, having a rotatable shaft; torque means for coupling said rotatable shaft to said friction pad means for developing a torque on said friction pad means urging the same to rotate relative to said frame element and hence the surface under test; said torque means forming a coupling between said rotatable shaft and said friction pad means which permits rotation of said rotatable shaft to occur without rotation of said friction pad means below torque values representative of static friction torque sensing means for sensing the torque developed by said torque means; and speed sensing means for sensing the rotation of said friction pad means relative to said frame element and hence the surface under test.

2. The apparatus recited in claim 1, wherein said friction pad means is connected to said motor through the means of a fluid coupling.

3. An apparatus for measuring and testing coefficient of friction characteristics of a surface and the like, the apparatus comprising: an outer frame adapted to be fixed relative to the surface under test; friction pad means mounted rotatably relative to said outer frame and adapted to contact the surface under test; torque means for developing a torque on said friction pad means urging the same to rotate relative to said frame element and hence the surface under test; torque sensing means for sensing the torque developed by said torque means; and speed sensing means for sensing the rotation of said friction pad means relative to said frame element and hence the surface under test; wherein said torque sensing means includes means for enabling said motor to angularly displace relative to said outer frame.

4. The apparatus recited in claim 3, wherein the angular displacement of said motor is sensed by passing light through a coded torque reticle.

5. An apparatus for measuring and testing coefficient of friction characteristics of a surface and the like, the apparatus comprising: an outer frame adapted to be fixed relative to the surface under test; friction pad means mounted rotatably relative to said outer frame and adapted to contact the surface under test; torque means for developing a torque on said friction pad means urging the same to rotate relative to said frame element and hence the surface under test; torque sensing means for sensing the torque developed by said torque means; and speed sensing means for sensing the rotation of said friction pad means relative to said frame element and hence the surface under test; wherein the rotation of said friction pad means is sensed by passing light through a coded speed reticle.

6. The apparatus recited in claim 1, and further comprising leveling means for enabling said friction pad means to take a position in the plane of the surface under test.

7. The apparatus recited in claim 1, and further comprising vertical adjustment means to enable said friction pad means to move relative to said outer frame in a direction parallel to its axis of rotation.

8. The apparatus recited in claim 1, and further comprising control means for controlling the speed of rotation of said friction pad means relative to said outer frame.

9. The apparatus recited in claim 8, wherein the speed of rotation of said friction pad means is controlled in accordance with a predetermined schedule.

10. A method for measuring and testing the coefficient of friction characteristics of a surface and the like, the method comprising the steps of: placing a rotatable friction pad means in physical contact with the surface under test; developing a torque on said friction pad means urging the same to rotate relative to the surface under test, but insufficient to cause rotation; increasing the torque until said friction pad means rotates relative to the surface under test; and sensing the magnitude of said torque at the instant said friction pad means began its rotation.

11. The method recited in claim 10, wherein said torque is developed by a motor associating with said friction pad means.

12. The method recited in claim 9, wherein said motor associates with said friction pad means through a fluid coupling.

13. The method recited in claim 10, and further comprising the steps of measuring and testing dynamic coefficient of friction characteristics by increasing the rotational speed of said friction pad means relative to the surface under test, sensing the torque developed at various speeds during said increase, and sensing said various speeds during said increase.

14. A method for meauring and testing the coefficient of friction characteristics of a surface and the like, the method comprising the steps of: placing a rotatable friction pad means in physical contact with a surface; imparting a torque on said friction pad means, insufficient to cause rotation thereof; increasing said torque so as to cause said friction pad means to rotate while in contact with said surface; and measuring coefficient of friction characteristics between said friction pad means and said surface while said friction pad means is rotating.

* * * * *